US008600483B2

(12) United States Patent
Mintz et al.

(10) Patent No.: US 8,600,483 B2
(45) Date of Patent: Dec. 3, 2013

(54) MOBILE IN VIVO INFRA RED DATA COLLECTION AND DIAGNOSES COMPARISON SYSTEM

(75) Inventors: Frederick W. Mintz, Chatsworth, CA (US); Philip I. Moynihan, La Canada, CA (US); Sarath D. Gunapala, Stevenson Ranch, CA (US)

(73) Assignee: California Institute of Technology, Pasadena, CA (US)

( * ) Notice: Subject to any disclaimer, the term of this patent is extended or adjusted under 35 U.S.C. 154(b) by 1005 days.

(21) Appl. No.: 12/214,553

(22) Filed: Jun. 18, 2008

(65) Prior Publication Data
US 2009/0012402 A1    Jan. 8, 2009

Related U.S. Application Data

(63) Continuation-in-part of application No. 11/726,403, filed on Mar. 20, 2007.

(60) Provisional application No. 60/783,938, filed on Mar. 20, 2006, provisional application No. 60/936,046, filed on Jun. 18, 2007.

(51) Int. Cl.
*A61B 6/00*         (2006.01)
(52) U.S. Cl.
USPC ........................................................ 600/473
(58) Field of Classification Search
USPC ........................................................ 600/473
See application file for complete search history.

(56) References Cited

U.S. PATENT DOCUMENTS 3,486,169 A * 12/1969 Rawlings ........................... 2/414

| 5,090,415 | A | * | 2/1992 | Yamashita et al. ............ | 600/476 |
|---|---|---|---|---|---|
| 5,273,037 | A | | 12/1993 | Itil et al. | |
| 5,823,832 | A | | 10/1998 | Das | |
| 6,675,600 | B1 | * | 1/2004 | Robillard et al. ............ | 62/259.2 |
| 7,087,075 | B2 | * | 8/2006 | Briscoe et al. ................ | 607/104 |
| 2001/0018554 | A1 | * | 8/2001 | Yamashita et al. ............ | 600/178 |
| 2002/0027649 | A1 | * | 3/2002 | Chudner ......................... | 356/39 |

(Continued)

FOREIGN PATENT DOCUMENTS

WO    WO 03/005897    1/2003

OTHER PUBLICATIONS

PCT International Search Report and the Written Opinion of the International Searching Authority for PCT/US2007/011710.

(Continued)

*Primary Examiner* — Long V. Le
*Assistant Examiner* — Bo J Peng
(74) *Attorney, Agent, or Firm* — Tope-McKay & Associates

(57) ABSTRACT

Described is a mobile in vivo infrared brain scan and analysis system. The system includes a data collection subsystem and a data analysis subsystem. The data collection subsystem is a helmet with a plurality of infrared (IR) thermometer probes. Each of the IR thermometer probes includes an IR photodetector capable of detecting IR radiation generated by evoked potentials within a user's skull. The helmet is formed to collect brain data that is reflective of firing neurons in a mobile subject and transmit the brain data to the data analysis subsystem. The data analysis subsystem is configured to generate and display a three-dimensional image that depicts a location of the firing neurons. The data analysis subsystem is also configured to compare the brain data against a library of brain data to detect an anomaly in the brain data, and notify a user of any detected anomaly in the brain data.

18 Claims, 7 Drawing Sheets

(56) References Cited

U.S. PATENT DOCUMENTS

| | | | |
|---|---|---|---|
| 2002/0049389 A1* | 4/2002 | Abreu | 600/558 |
| 2003/0009286 A1* | 1/2003 | Shibusawa et al. | 702/2 |
| 2003/0103037 A1* | 6/2003 | Rotzoll | 345/157 |
| 2003/0190066 A1* | 10/2003 | Boas et al. | 382/131 |
| 2004/0076316 A1* | 4/2004 | Fauci | 382/128 |

OTHER PUBLICATIONS

PCT International Preliminary Report on Patentability for PCT/US2007/011710.

* cited by examiner

MOBILE IN VIVO INFRA RED DATA COLLECTION AND DIAGNOSES COMPARISON SYSTEM

PRIORITY CLAIM

The present application claims the benefit of U.S. Provisional Application No. 60/936,046, filed Jun. 18, 2007; the present application is also a continuation-in-part of prior application Ser. No. 11/726,403, filed on Mar. 20, 2007, which claims the benefit of U.S. Provisional Application No. 60/783,938, filed on Mar. 20, 2006.

STATEMENT OF GOVERNMENT INTEREST

The invention described herein was made in the performance of work under a NASA contract, and is subject to the provisions of Public Law 96-517 (35 USC 202) in which the Contractor has elected to retain title."

BACKGROUND OF THE INVENTION (1) Field of Invention

The present invention relates to a brain data analysis system and, more specifically, to a mobile in vivo infra red brain scan system that is configured to collect remote and mobile data of brain activity for real-time analysis.

(2) Description of Related Art

Historically, human-brain dysfunctions have been diagnosed by psychiatric and psychological professionals in terms of behavioral characteristics. This approach to diagnoses catalogs the incidences of observed behavior in statistical correspondence to those listed in the Diagnostic and Statistical Manual of Mental Disorders, Fourth Edition (DSM). Better known as the DSM-IV-TR, the manual is published by the American Psychiatric Association and covers all mental health disorders for both children and adults. It also lists known causes of these disorders, statistics in terms of gender, age at onset, and prognosis as well as some research concerning optimal treatment approaches. The Manual is re-published about every five years. It establishes standard definitions of pathologic behavior but, over the years, often substantially changes the definitions of abnormal vs. normal behavior.

Therapies carried out by professional clinicians range from permanent institutionalization through in-patient hospital treatment to various, out-patient behavior modification techniques. Often, psychiatric physicians prescribe chemical drug therapies in order to modify or manage symptomatic behavior. These drugs are meant to alter neuro-chemical activity in the brain. Validation of the efficacy of these drug treatments is, however, still observational. Although these clinicians may carry out a protocol of pre- and post-therapy blood tests to ascertain metabolic balances juxtaposed against behavioral changes, the diagnoses are still observational and subjective. This approach to diagnosis defines the "Subjective versus Objective Problem." What is needed is a more scientific approach to diagnosis than observation-based determinations.

It is generally recognized that upwards of 80 percent of all neuro-scientists have existed only in the past 30 years. It has only been within the past 15 years that sophisticated brain imaging techniques have been invented and used in attempts to inform researchers and clinicians about brain activity versus behavior. The discovery of "brain waves" is attributed to Richard Canton, an English researcher in the year 1875. Electro-Encephalography (EEG) as a technique for detecting brain activity in humans and is attributed to Hans Berger in the year 1929. Modern brain imaging techniques date from the mid-1970's, with the advent of Magnetic Resonance imaging (MRI). The current state-of-the-art for brain imaging is called function Magnetic Resonance Imaging (fMRI).

Imaging (fMRI) combines the sum of constructs of evoked potential events (at the bundled synapses level) with the static images of an MRI image. However, fMRI is not a mobile, physical activity related, real-time diagnostic tool. In other words, while fMRI provides data related to sight, sound, and some thought, it confines the user to a large machine and does not provide for brain analysis while moving. Thus, current fMRI techniques do not provide for an analysis during the range of human behaviors, particularly for children and adults with serious behavioral or mental problems.

The overwhelming complexity of the mammalian brain, juxtaposed against the current (noninvasive) state-of-the-art in brain imaging, associated with scientifically characterizing various brain activities, still defines the "Objective versus Subjective Problem." Thus, what occurs in the brain from a physiological and chemical point of view, relating to active physical and psychological behavior, is still largely unknown. The reason for most of the imprecise diagnoses is due to "The Subjective versus Objective Problem."

The substantial overlap of observed behaviors, characterized in the List of Clinical Syndromes, Developmental, and Personality Disorders in the DSM, is legion. It is estimated by some researchers that more than 25 percent of the World's population suffers from mental/emotional problems. It is also estimated that 47 percent of those requiring interventional mental care do not receive it. More than 28 percent of the Member Nations of the World Health Organization do not have budget items for mental health. Even in countries like the United States of America, the statistics seem ineluctable. Most of the mentally disabled do not receive effective intervention therapies due to well-recognized and closely related problems, such as poverty, lack of medical insurance coverage, and inaccurate diagnoses.

Currently, scientific studies relating to the brain take place primarily in university departments of medicine, biology, psychology, engineering, information science, philosophy, and (interestingly) music. The wide range of these academic research interests is beginning to generate a growing amount of much needed, interdisciplinary research and data sharing.

In addition to the need to more precisely define the standardized diagnoses cataloged in the DSM, there is a need to study the neuronal activity of the brain in real-time as it responds to a wide range of internal and external stimuli (as described further below). There is a need, for instance, to study the impact of psychological and physical trauma on the developing brain. Additionally, there is a need for brain studies of high-risk job candidates, such as astronauts to qualify them for space flight as well as astronauts working in outer space. Further, there is an urgent need to study the possible causes and results of a broad range of Autistic Spectrum Disorders in adults and children.

The central and peripheral nervous systems are marvelous detector systems for sensing minuscule changes in the external environment in which the human body exists. In many respects, the human auditory, visual, and olfactory systems are far more sensitive than our most sensitive detector instruments. Indeed, the human eye can detect changes of a single photon! The olfactory bulbs and auditory processing systems in the brain are similarly sensitive. However, the integration and processing times, necessary to become consciously aware of these sensory inputs, is often dangerously long. This is because our own, "experiential training," inhibits the conscious compilation of these data in the prefrontal cortex, which is where they are first evaluated against memorized experiences in frontal cortex and then sent back to other parts of the brain to "take action."

This is why external stimuli (such as potentially dangerous sights, sounds, smells, movements, skin pressure) and all of the other external somatosensory inputs, as well as dysfunctional internal sensory stimuli (such as an irregular heartbeat, breathing, blood pressure, planar orientation, gravity etc., carried by the proprioceptive nervous system) are largely "ignored," until it is consciously decided that they have become too critical. Humans cannot detect (at the conscious level) most of these "early warning signals." Humans have learned, over millions of years, to ignore many of these minute stimuli in favor of adapting to or modifying the surrounding environment. This may explain why animals are far more sensitive to external stimuli; because they have not learned to ignore or modify environmental change like humans (e.g., the recent tragic tsunami events in the Far East, where all of the indigenous animals ran inland long before the first tsunami hit the beaches).

Thus, when things begin to "go wrong" on Earth or in Outer Space, they often start as a small anomaly; like the distant, imperceptible roar of sounds in the sea (a precursor to a tsunami), or a low frequency, slowly moving ground wave (a precursor of an earthquake), or the small reduction in pressure on the human skin (like the beginning of a crack/leak in a space suit). All of these small anomalies induce subtle neuronal changes, which the Central Nervous System (CNS) will detect and record long before the Earth bound or spacecraft instruments or commercial environmental safety systems, calibrated to "acceptable ranges," detect such dangerous stimuli.

Therefore, in addition to the reasons listed above for detecting and monitoring psychological conditions, there is an urgent need to detect and accurately identify, in real-time, brain related physiological anomalies and disabilities.

SUMMARY OF INVENTION

The present invention is a mobile in vivo infrared brain scan and analysis system. The system includes a helmet with a plurality of infrared (IR) thermometer probes. Each of the IR thermometer probes has an IR photodetector capable of detecting IR radiation generated by evoked potentials within a user's skull. While wearing the helmet, a user can collect in vivo brain data.

Additionally, each of the IR thermometer probes is affixed with the helmet using a mounting cap assembly. The mounting cap assembly houses a pressure-apparatus that is formed to force the IR thermometer probe away from the mounting cap assembly and toward a user's scalp.

The helmet further comprises shock absorbing pads and a chin strap to stabilize the helmet while worn by a user.

Additionally, a cold finger is attached with the IR photodetector, with a cold source passing through the mounting cap assembly and attached with the cold finger to cool the cold finger and thereby cool the IR photodetector.

The IR thermometer probe further includes an optical window in alignment with the IR photodetector for passing IR radiation to the IR photodetector. The IR thermometer probe is configured to acquire data and send it along signal wires to a Signal Processor and Transmitter. The Signal Processor and Transmitter is formed to transmit data to a data analysis subsystem.

The present invention further comprises a data analysis subsystem. The data analysis subsystem is configured to receive brain data from the helmet with a plurality of infrared (IR) thermometer probes. The brain data is reflective of firing neurons in a mobile subject. The data analysis subsystem is further configured to generate and display a three-dimensional image that depicts a location of the firing neurons.

In another aspect, the data analysis subsystem is further configured to compare the brain data against a library of brain data to detect an anomaly in the brain data (the anomaly being indicative of an abnormal brain function). The data analysis subsystem is also configured to notify a user of any detected anomaly in the brain data.

In yet another aspect, the data analysis subsystem further comprises a receiver system and a data processing system. The receiver system is configured to receive the transmitted brain data from the data collection subsystem. The data processing system has a relational database management system (RDBMS) controller for connecting with and operating an RDBMS having a library of brain data, and further being configured to receive the brain data from the receiver system and compare the brain data to the RDBMS to detect an anomaly in the brain data.

In another aspect, the data analysis subsystem is further configured to compare a detected anomaly in the brain data with an RDBMS to generate a diagnosis of the detected anomaly.

Additionally, the data analysis subsystem is further configured to compare the three-dimensional image with a RDBMS having a library of three-dimensional images to detect an anomaly in the brain data.

As can be appreciated by one skilled in the art, the present invention also comprises a method for forming and using the system described herein. The method for using the system comprising a plurality of acts for performing the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
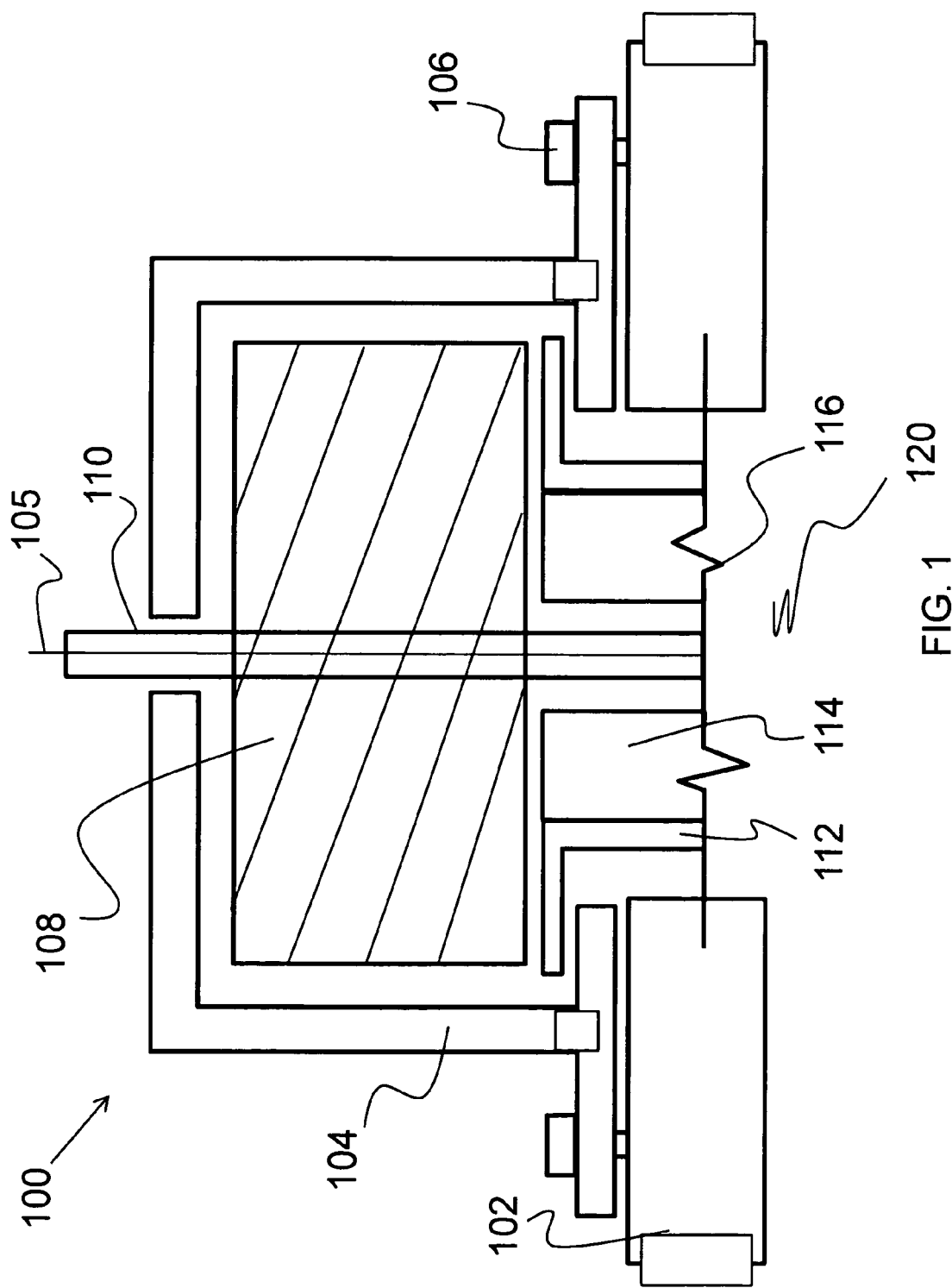
FIG. 1 is a cross-sectional view of mounting cap assembly for an infrared (IR) thermometer probe according to the present invention.

The present invention relates to a brain data analysis system and, more specifically, to a mobile in vivo infra red brain scan system that is configured to collect remote and mobile data of brain activity for real-time analysis. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

(1) Introduction

As noted above, the present invention relates to mobile in vivo infra red brain scan and analysis system. In operation, the present invention requires a mobile infra red data collection subsystem and a data analysis subsystem. The present invention, when fully implemented, can be deployed in a typical helmet (e.g., bicycle helmet) and image brain activity in real-time (e.g., microseconds). The brain activity can be imaged with excellent spatial resolution (e.g., millimeters) and displayed as three-dimensional data on a translucent model. Additionally, the images can be stored and compared with existing international relational data bases (RDBMS) with other function Magnetic Resonance Imaging (fMRI) images containing associated physiological and psychological diagnoses. For clarity, the infra red data collection subsystem will be described first, with the data analysis subsystem thereafter described.

(2) Infra Red Data Collection Subsystem

As described above, the present invention utilizes an infrared (IR) data collection subsystem that is formed to collect brain activity in real-time and transmit that data to a remote site for further analysis. As can be appreciated by one skilled in the art, the IR data collection subsystem is operable for gathering brain data from a mobile subject and transmitting that data to a remote site. Thus, the IR data collection subsystem illustrated in FIGS. 1 through 6 provides a non-limiting example of a suitable device for operation with the present invention.

As discussed above, the IR data collection subsystem can be incorporated into a helmet. As shown in FIG. 1, the IR data collection subsystem includes a mounting cap assembly 100 for mounting the IR thermometer probe (illustrated in FIG. 2 as element 120) with a helmet 102. The mounting cap assembly 100 includes a mounting cap 104 that is attached with the helmet 102 using a probe fastener 106. The probe fastener 106 is any suitable mechanism or device for attaching one object with another, a non-limiting example of which includes a screw-type mechanism (e.g., threaded screw).

Encased within the mounting cap assembly 100 is a pressure-apparatus 108 for forcing the IR thermometer probe 120 towards a user's scalp. The pressure-apparatus 108 is any suitable mechanism or device that includes expansive properties when compressed, a non-limiting example of which includes a compression spring (e.g., having a spring constant on the order of 0.5 pounds/inch).

A cold source 110 is passed through the mounting cap 104 to the IR thermometer probe 120. The cold source 110 is any suitable mechanism, device, technique, or system for transmitting a temperature to a particular point or object, a non-limiting example of which includes a refrigerant attached with a metallic wire, with the metallic wire operating as the cold source 110 and passing through the mounting cap 104 to the IR thermometer probe 120.

Also depicted in FIG. 1 are the probe outer wall 112 (formed of Titanium or other low-conductivity material) and an upper segment of a low-conductivity housing 114 of the IR thermometer probe 120. For clarity, FIG. 1 also depicts the interface 116 to the IR thermometer probe 120.

Figure 2:
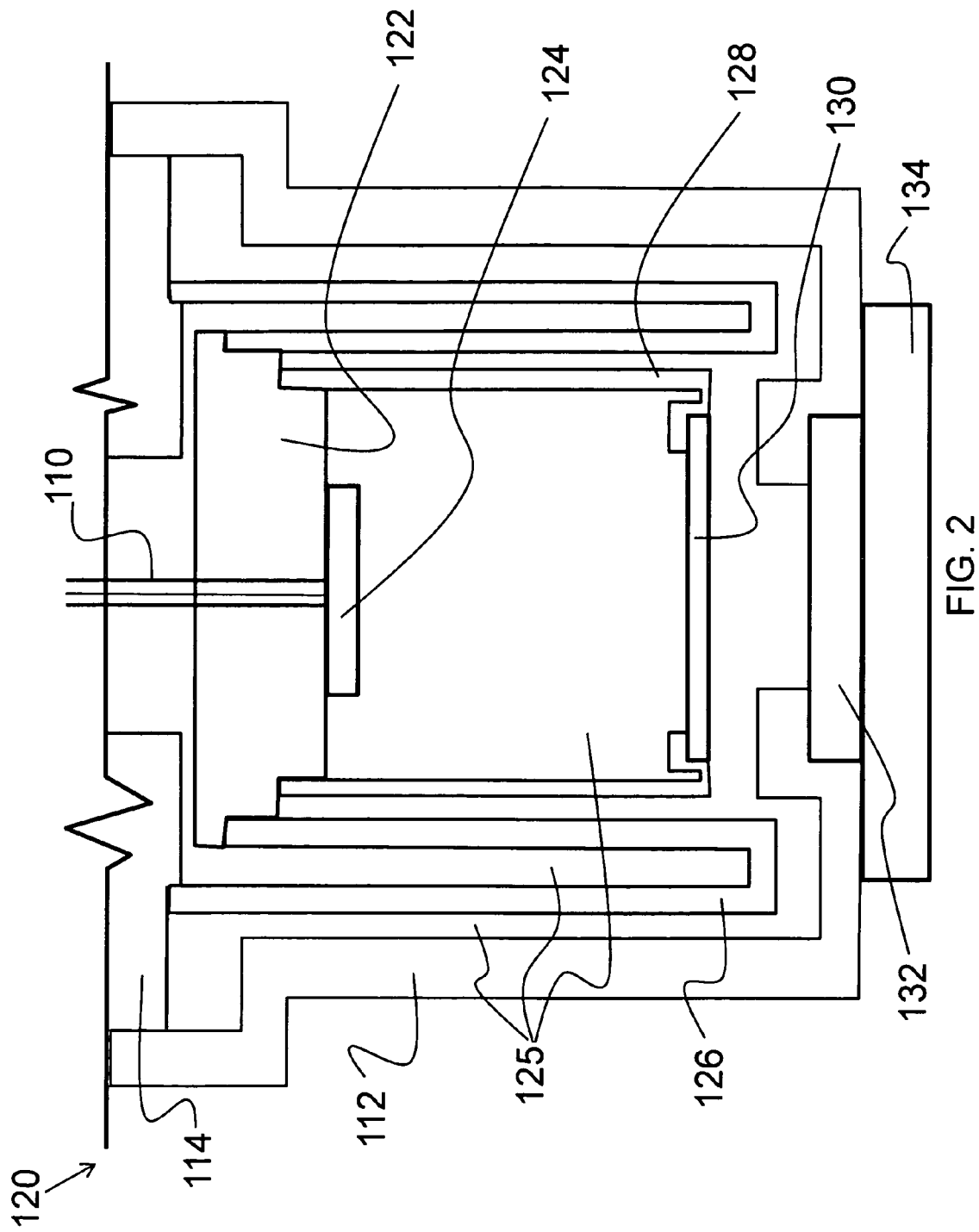
FIG. 2 is a cross-sectional view of an (IR) thermometer probe according to the present invention.

FIG. 2 illustrates a cross-sectional view of an IR thermometer probe 120 according to the present invention. The probe outer wall 112, the low-conductivity housing 114, and the cold source 110 can also be seen within the context of the IR thermometer probe 120. As shown, the cold source 110 continues to a cold finger 122 which distributes the temperature provided by the cold source 110 to an IR photodetector 124. As a non-limiting example, the cold finger 122 is a thermoconductive plate (e.g., metal). The IR photodetector 124 is any suitable mechanism or device that converts infrared energy to an electrical signal that can be measured as units of temperature (after being adjusted for ambient temperature variation). Non-limiting examples of the IR photodetector 124 include a Gallium Arsenid (GaAs), Indium Antinomide (InSb), or other IR chips, cooled by a small Sterling Engine (i.e., cold finger 122) mounted contiguous to, but isolated from the mounting cap assembly 100 (for thermal isolation from the skull). The IR photodetector 124 can also include quantum well infrared photodetector (QWIP) sensitivity.

The IR thermometer probe 120 also includes several spaces of evacuated volume 125; within the probe outer wall 112; within a low-conductivity support structure 126; and within an internal wall 128 and between the IR photodetector 124 and a cold filter 130. The cold filter 130 is nay suitable mechanism or device for filtering a temperature, a non-limiting example of which includes Zinc Selenide or Germanium.

The mounting cap assembly 100 is mounted (in multiple rows and columns) on the inside of the shock layer of a typical bicycle helmet (element 102 in FIG. 1). In other words, in order to work as an infrared brain scan system, the present invention includes a plurality of mounting cap assemblies 100, each with an IR thermometer probe 120.

Below the IR photodetector 124 is an optical window 132. The optical window 132 is an IR transmissive optical window that is made of low-conductivity material and capable of transmitting IR radiation. A gel 134 or other thermoconductive material can be placed on the users scalp to facility the transfer of IR radiation to the IR thermometer probe 120.

Flexible data leads or cables from the IR photodetector 124, exit from the top of the spring-loaded mounting cap assembly 100 (providing smooth contact with the subject's scalp) to connect with a multi-channel radio-frequency (RF) transmitter which is, in turn, connected to patch antenna(s) on the outside of the helmet. These multiple data are transmitted to a remote site where they are processed by software to present a three-dimensional display of evoked potentials in the subject brain (representing firing neuronal bundles) indicating the location of neuronal activity associated with mental or physical activity. Further, they are available, in real-time, to be compared to relational data bases (RDBMS) existing in universities and research centers internationally.

Figure 3:
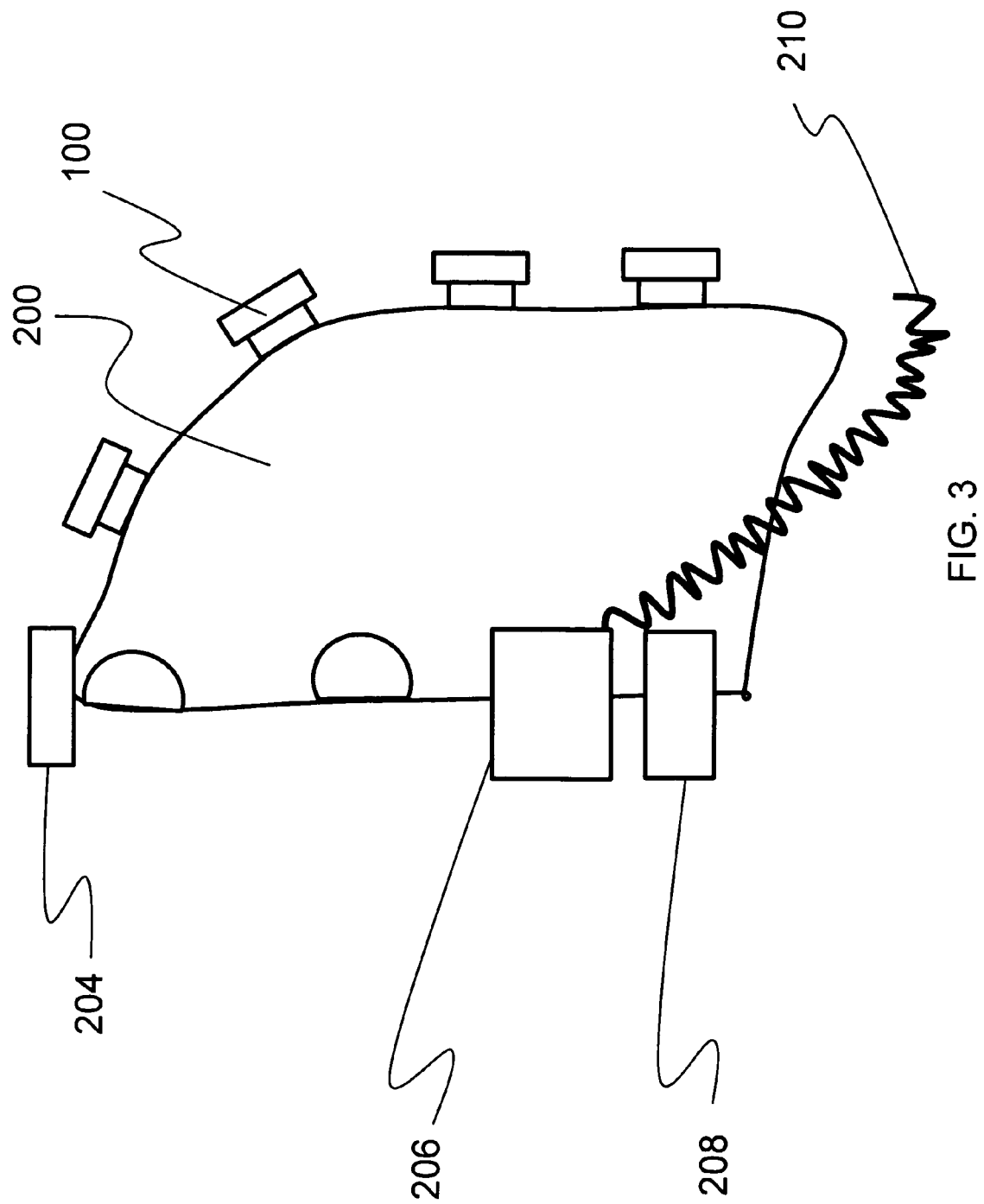
FIG. 3 is a cross-sectional, rear-view of a helmet, illustrating an IR thermometer probe attached with a helmet according to the present invention.
Figure 4:
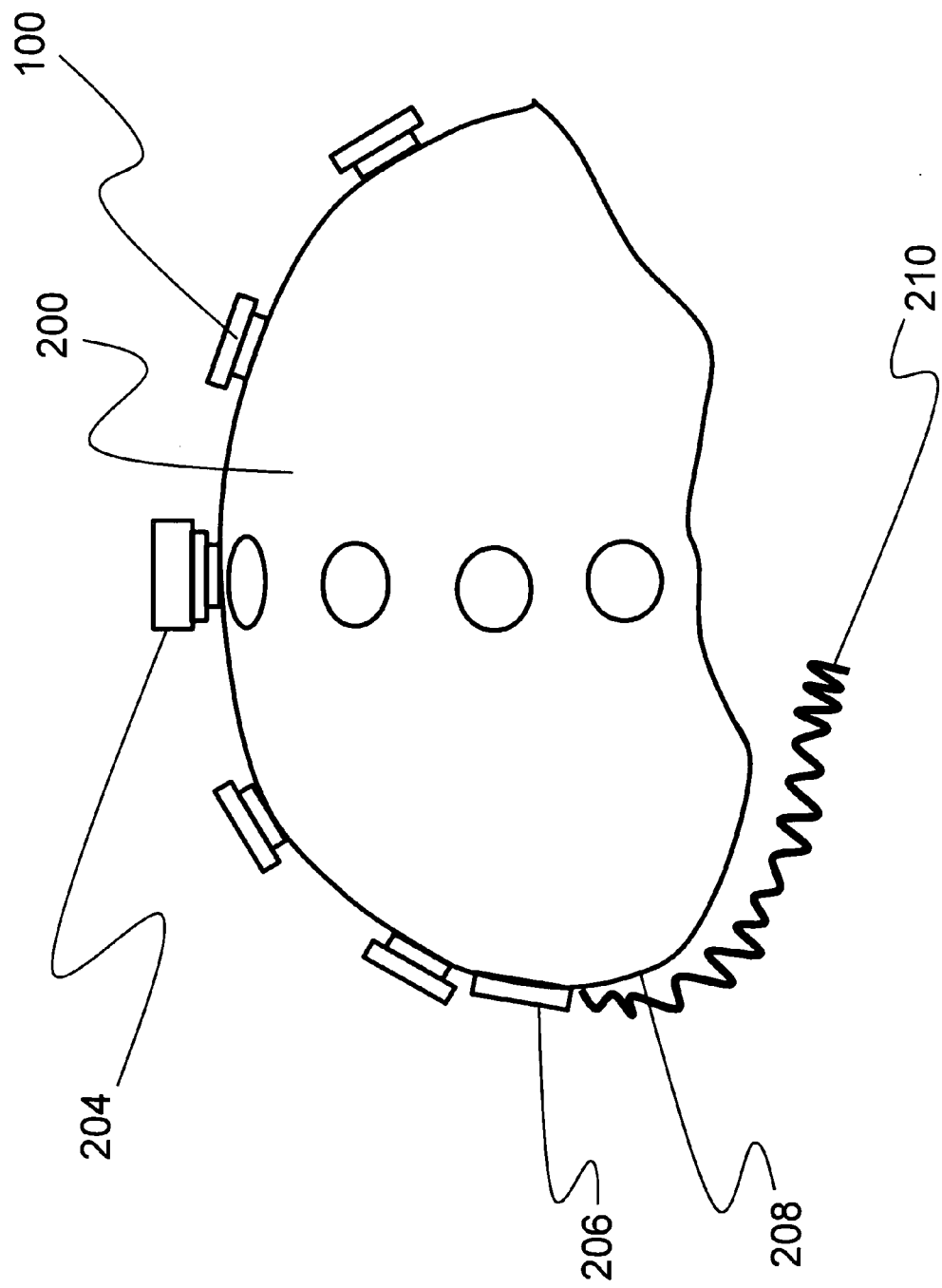
FIG. 4 is a right, side-view of the helmet according to the present invention.
Figure 5:
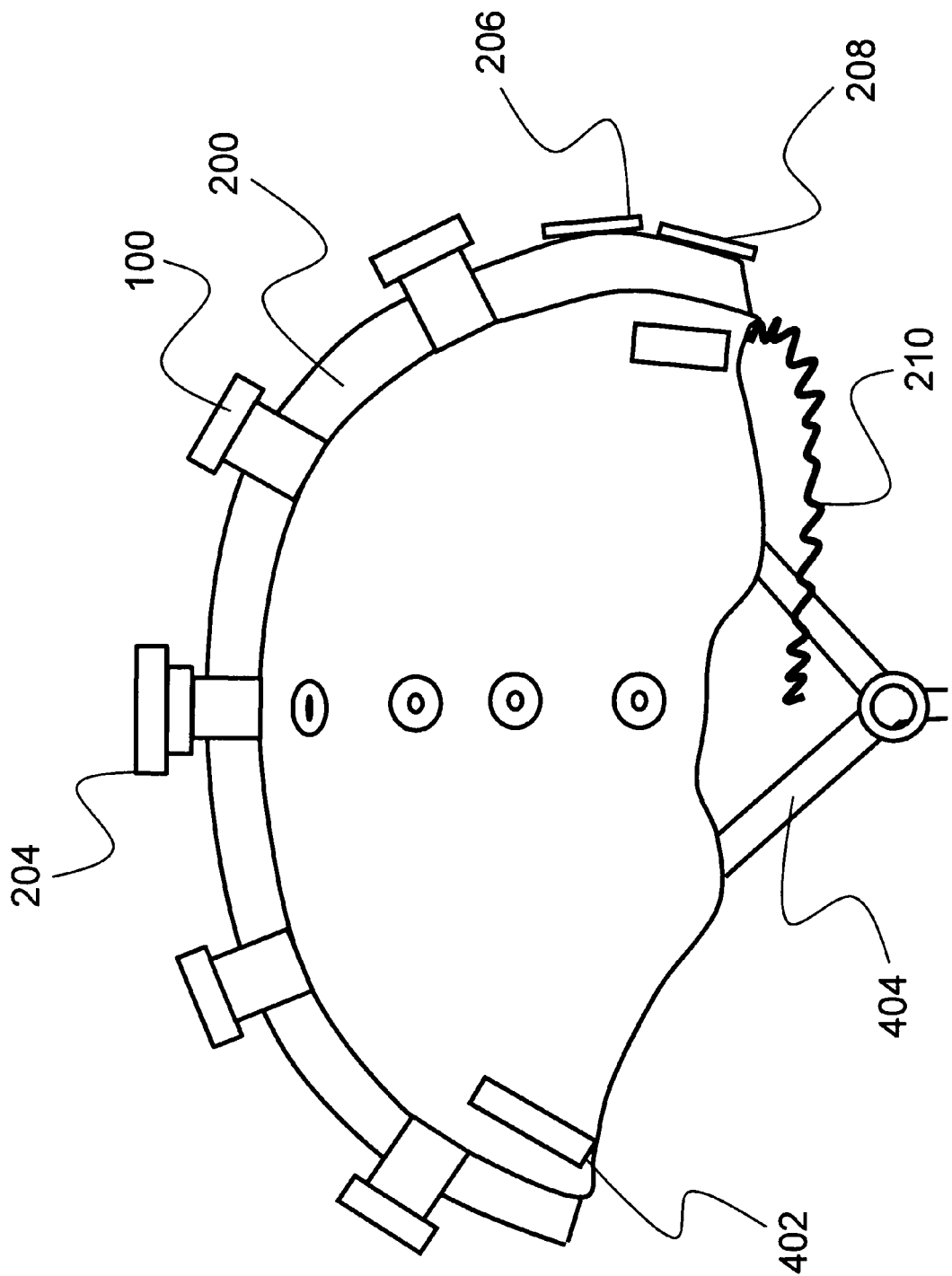
FIG. 5 is a cross-sectional, left side-view of the helmet according to the present invention.

As can be appreciated by one skilled in the art, a sole IR thermometer probe 120, in of itself, does not enable a user to capture useful brain data. Thus, the present invention also includes a helmet with a shock absorbent lining for attaching to a user's scalp. FIGS. 3 through 5 depict various views of a helmet's shock lining 200 according to the present invention. The shock lining 200 is any suitable material that allows a user to affix a plurality of mounting cap assemblies 100 (and corresponding IR thermometer probes) to the user's scalp, a non-limiting example of which includes a standard bicycle helmet. To facilitate in vivo usage, the shock lining 200 includes shock-absorbing pads 402 and a chin-strap 404 to stabilize the shock lining 200, which stabilizes the mounting cap assemblies 100.

As described in further detail below, the present invention also allows the system to transmit the multiple channel evoked potential data to a remote location, such as a Receiver Data Processor System, a non-limiting example of which includes the aforementioned RDBMS. To enable such a transmission, a plurality of signal wires (shown as element 105 in FIG. 1) transfer the data from the individual mounting cap assemblies 100 to a Signal Processor and Transmitter 206, as shown in FIGS. 3 through 5. Data will be transferred from the transmitter by use of any suitable transmission device, such as a patch antenna 204 mounted on the outside of the helmet. Additionally, the mobile IR brain scan system (helmet shock lining 200, multiple mounting cap assemblies 100 (and corresponding IR thermometer probes), and requisite components) will be powered by a rechargeable or replaceable battery 208 or any other suitable power source. A common ground lead 210 will be required which will serve as a reference for all recorded brain data.

Figure 6:
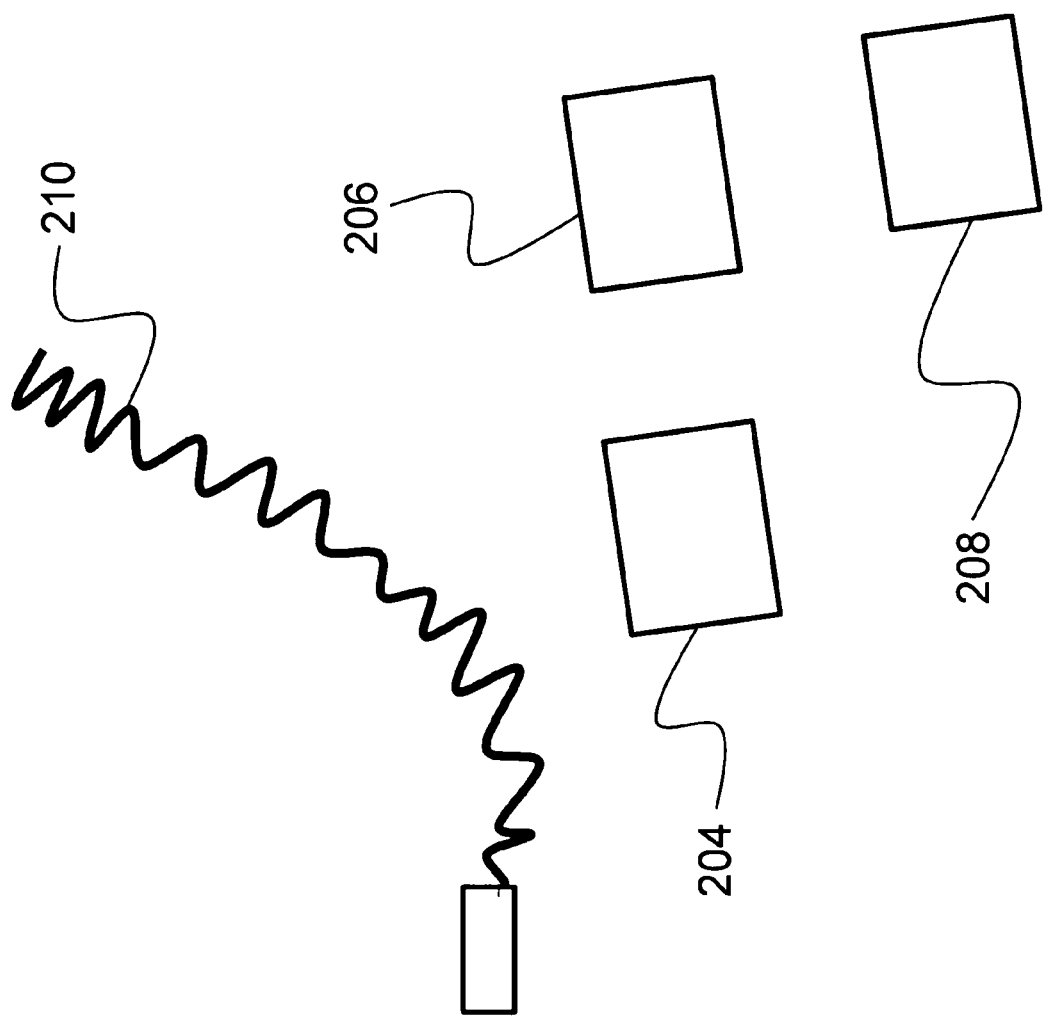
FIG. 6 is an exploded-view of components of the present invention.

FIG. 6 further illustrates some of the important electronics utilized in the system, including the analog-to-digital Signal Processor and multiple channel Transmitter 206, the patch antenna 204 for placement outside the helmet, the battery 208, and the common ground lead 210.

As a further description, the spring-loaded, IR thermometer probe 120 is assembled into a small cylinder (i.e., probe outer wall 102) and is mounted in the shock-absorber lining of a helmet (described in further detail below). One or more of these cylinders will be used in the system.

In a desired aspect, these cylinders (e.g., typically 1.5 centimeters (cm)×1.5 cm in diameter) are mounted in such a way and in such numbers as to effectively replicate the typical placement and distribution of the standard, paste-on EEG probes used in medical and clinically based settings (or in current ambulatory EEG systems). The evoked electromotive force (EMF) wave potentials, generated from firing neuronal bundles in the brain, are picked up by these "floating" sensor probes and carried by small, insulated cables to a miniaturized multi-channel processor and radio-frequency (RF) transmitter inside the helmet and connected to typical Patch Antennas affixed to the outside surface of the helmet. Signal sampling rates can be on the order of microseconds so as to detect the multiple locations of sequentially firing neurons. These transmitted signals are received at a remote site for further processing into three-dimensional images, depicting the location of the firing neuronal bundles in three-dimensional (3D) space, and are superimposed on a graphically depicted translucent brain model matching the size of the subject under study. The processed signals and images are then downloaded to the relational database management system (RDBMS) for further study, analysis, and comparison with other similar data.

In another aspect, the EEG (EMF) data or other evoked brain potential data are collected by each of the IR thermometer probes 120 will be passed through the small wire bundle to the helmet Signal Processor and Transmitter. The collected data is then transmitted by the small RF Transmitter to a remote location where it is downloaded into a computerized data base for further inspection, normalization, and preparation for comparison to similar data in International Brain Data Base Systems.

(3) Data Analysis Subsystem

As noted above, the present invention also includes a data analysis subsystem that is configured to receive the brain data at a remote site for further processing. For example, the system is configured to display the data in a visual, 3D format that will enable diagnostic professionals to identify the precise neural-physiological sources and transmission patterns of the firing neurons in real-time, which will greatly improve the understanding of the actual function of the brain as relates to actual physical and psychological behavior. It should be noted that although the present invention is described as being used with EEG data and other evoked potential brain data, it is not intended to be limited thereto as the data collection and analysis aspects of the present invention can be used with any measurable data that is representative of brain function.

As described above, the present invention relates to a system for mobile brain data collection, analysis, and 3D display of firing neurons in the brain, otherwise known as evoked potentials. The system utilizes IR thermometer probes (an example of which is described above) that are capable of the automatic collection IR brain data. The present invention is also capable of collecting and analyzing the acquired data. In this aspect, neural activity, in the form of evoked field potentials and electromotive force (EMF) signals, will be recorded simultaneously from multiple channels. The data is transmitted to a remote site for further analysis of the raw data (as is usually done by a neurologist) and then processed by time-domain software into a 3D display of the location of firing neurons. The acquired data will be become part of a RDBMS for brain data and will be professionally analyzed on a time-scale that approaches real-time or near-real-time.

The present invention includes an automated diagnosis system as part of the RDBMS. Thus, the present invention includes a data analysis system that provides a means for a peer-review approach to the analysis and comparison of brain data with other (e.g., international) RDBMS systems which contain similar data. The analysis and comparison of these brain-wave patterns and corresponding images can be made available for study by trained medical professionals or compared to other, similar signals and images and associated diagnoses located in RDBMS's at similar international research locations.

Figure 7:
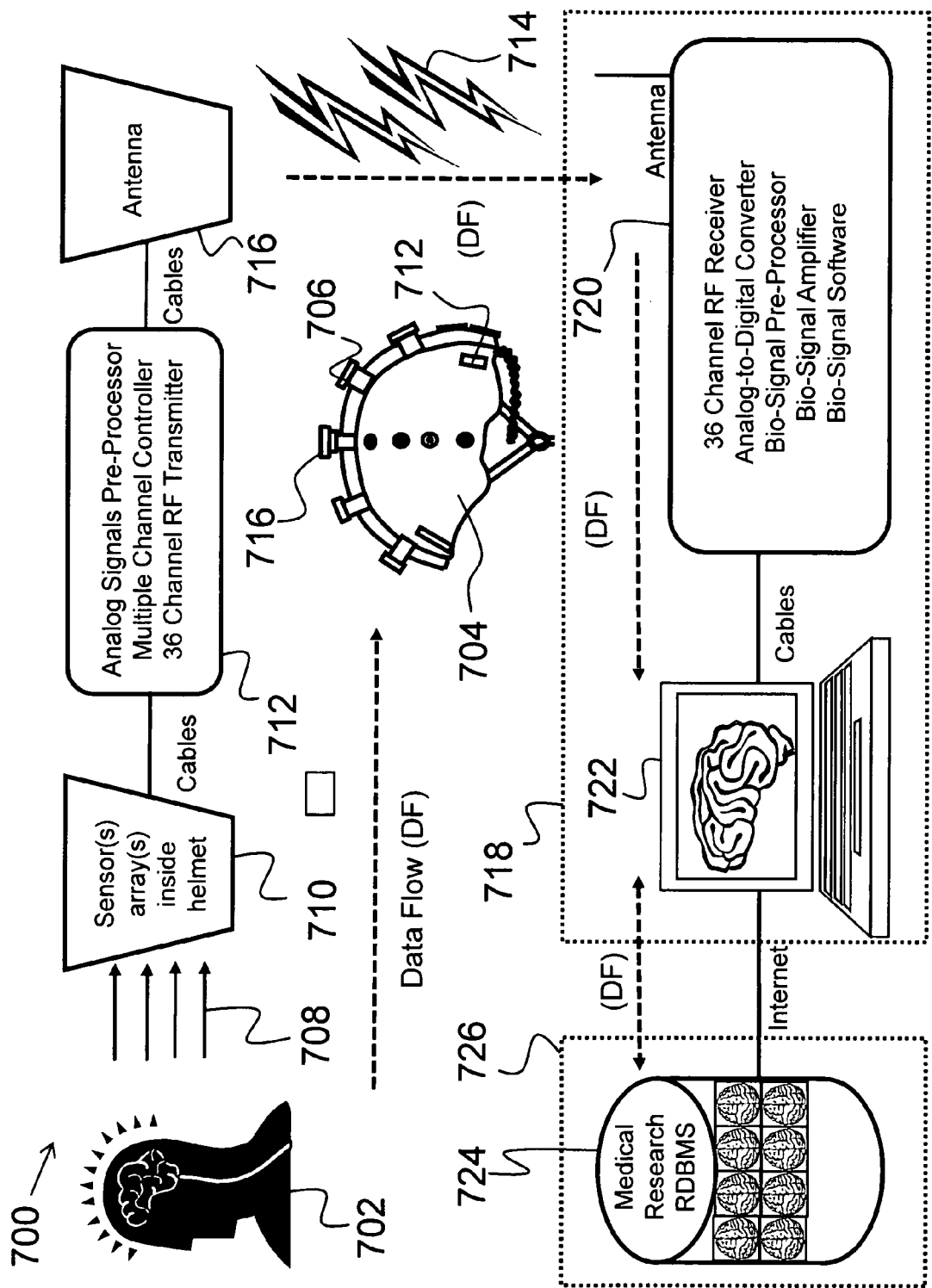
FIG. 7 is a data flow diagram of a mobile in vivo IR brain scan system according to the present invention.

FIG. 7 illustrates the components and data flow of the mobile in vivo IR brain scan and analysis system 700 according to the present invention.

As shown, a mobile subject 702 under study is provided with a helmet 704 (or other suitable device) containing a plurality of IR thermometer probes 706. Neuron bundles in the mobile subject's 702 brain generate evoked potentials 708 which are captured by an array 710 of IR thermometer probes 706 positioned within the helmet 704. The evoked potentials 708 are then passed to a signal processor and transmitter 712.

The signal processor includes a digital-to-analog pre-processor and a multi-channel controller. The transmitter is any suitable mechanism or device for transmitting said signals, a non-limiting example of which includes a 36 channel radio frequency (RF) transmitter. Thus, the signal processor and transmitter 712 converts the digital signals into analog signals 714 and further transmits the signals 714 using an antenna 716 (e.g., a patch antenna attached on the outside of the helmet). The helmet 704, sensor array 710 (including probes 706), signal processor and transmitter 712, and antenna 716 collectively operate as a non-limiting example of a data collection system according to the present invention.

The signals 714 are then transmitted to the data analysis system. The signals 714 are captured at a remote site 718 using a receiver system 720. The receiver system 720 is any suitable mechanism or device capable of initially receiving the signals 714 and pre-processing the signals 714 for further processing. As a non-limiting example, the receiver system 720 includes a 36 channel RF receiver, an analog-to-digital converter, a bio-signal pre-processor, a bio-signal amplifier, and bio-signal software. The 36 channel RF receiver is used to receive the various signals 714 as transmitted by the RF transmitter. The analog-to-digital converter is used to convert the captured analog signals into digital signals.

The bio-signal pre-processor is used to prepare the signals to convert the analog EMF signals coming from the evoked potentials in the brain to digital signals used to transmit the data to the remote site. The bio-signal amplifier is used to amplify the signals for further processing. The bio-signal software is used for taking the 36 channels of data.

The receiver system 720 is connected with a data processing system 722 (e.g., computer) for further processing. The receiver system 720 can be incorporated into the same machine as the data processing system 722. The data processing system 722 includes 3D software and RDBMS controller for connecting with and operating an RDBMS 724. The RDBMS 724 is connected with the data processing system 722 through any suitable communicative connection, non-limiting examples of which include being directly hard-wired, being connected through the Internet, and a wireless connection. As discussed above, a desired aspect of the present invention is that it provides for the collection of data and access to that data remotely. Thus, it is desirable that the data processing system 722 is connected with the RDBMS 724 through the Internet, with the RDBMS 724 being at yet another remote site 726 (although in another aspect, the RDBMS 724 can be directly connected to the data processing system 722).

Additionally, it should be noted that although cables are listed as the connection device between several of the components illustrated in FIG. 7, the invention is not intended to be limited thereto as any other suitable communicative connection can be established between the various illustrated components, non-limiting examples of which include wireless and Bluetooth connections.

These signals are processed for transmission by a small integrated multi-channel transmitter to a remote site for further computer processing into three-dimensional (3D) images which show the location (with millimeter accuracy) and the sequential timing (in microseconds) of these firing neurons. The frequency and power of the small, helmet-integrated transmitter is designed within the narrow range of non-bio-harmful parameters. The 3D images are produced using any suitable signal interferometric technique. A non-limiting example of such a technique is the postulated Boundary Element Method, such as that described by Stefan F. Filipowicz in "Identification of the Internal Sources with the Aid of Boundary Element Method," as published at the International Workshop entitled, "Computational Problems of Electrical Engineering," Zakopane, Poland, 2004, which is incorporated by reference as though fully set forth herein.

Thus, the brain data (e.g., EEG data) can be used to construct 3D images of evoked potentials within the brain. As a non-limiting example, initially assuming homogeneity of the transport and diffusion mechanisms of the cellular structures under study, the governing equations are (1) Poisson's equation with (2) Neumann's boundary conditions, according to the following:

$$\nabla^2 u(\vec{r}) = -b(\vec{r}), \text{ and} \quad (1)$$

$$q(\vec{r}) \frac{\delta u(\vec{r})}{\delta n} = 0, \quad (2)$$

where u denotes electric potential, b denotes internal sources, and $\vec{r}$ denotes a position vector.

The discrete, individual, evoked potential data collected by the data collection subsystem can be presented in a 3D format using a postulated Boundary Element Method or some other method, such as the least squares method. As such, the present invention is configured to use the Boundary Element Method to mathematically model and depict the firing neuronal bundles in the brain, in 3D space, integrated with a semi-translucent model of the brain. In other words, the brain data is displayed in a 3D form, integrated with a semi-transparent or semi-translucent model of the brain as it approximates the subject's actual brain size, thereby improving 3D visualization.

The 3D images produced are comparable to and look similar to functional magnetic resonance imaging (fMRI), but in an active environment and in real-time. The data is collected while the subject is mobile and functioning in a normal work or play environment. This is to be contrasted with fMRI data collection techniques which require several minutes to obtain sufficient data for display. Thus, the subjects under study (in fMRI) must remain immobilized during the entire procedure. Alternatively, the present invention uses a remote, mobile, in vivo data collection subsystem which, in combination with the data analysis subsystem, can generate and display the relevant images in milliseconds, which is more consonant with the firing rate of neurons in the Central Nervous System (CNS).

The processed images are capable of inter-active, three-dimensional manipulation and examination. The processed data can be viewed in real time and also be compared with a library of brain data (such as a relational data base management system (RDBMS)), through the Internet, to similar data existing in international medical and research databases, such as the Laboratory on Neural Imaging (LONI) at the University of California, Los Angeles (UCLA), for comparison and validation of brain function diagnoses.

As can be appreciated by one skilled in the art, the present invention covers a wide range of brain imaging applications; such as medical triage events, physical, psychological, or other trauma.

The local and remotely controlled RDBMS 724 will allow for professional cooperative collaboration in the diagnosis of abnormal neural functioning that is indicative of pathology. For example, the brain data can be compared with a library of brain data to identify any anomalies in the brain data that may be indicative of a particular malady or pathology (abnormal brain function). Should such an anomaly be identified, it is possible to compare the anomaly with a database to diagnose the anomaly and notify the user of such an anomaly and/or diagnosis.

It is a goal of the present invention to create a system for both local-immediate and automated classification of, or hypothesis generation for, possible diagnosis of subjects under study 702. The automatic classification of acquired data having traits that are consistent with certain pathologies can be achieved by directly generating (through software) a classification using markers that are decided upon via a professional collaborative effort. An alternative is to build a system that employs some form of artificial intelligence or machine learning to perform the classification. Support Vector Machines, Bayesian Networks, and in general Knowledge Based Systems are examples of possible methods that allow a system to classify acquired data as being indicative of some pathology without the need to discreetly describe all of the classification rules.

In summary, the present invention comprises a new IR brain data collection system that allows for mobile, in vivo IR brain data collection, analysis, and diagnosis of EMF brain patterns. To accomplish this, evoked potentials (EEG), generated by firing neuronal bundles in the brain, are detected by the sensors (i.e., the data collection electrodes), gently riding on the surface of the scalp. These signals are processed for transmission by a small integrated multi-channel transmitter to a remote site for further computer processing into three-dimensional (3D) images which show the location (with millimeter accuracy) and the sequential timing (in microseconds) of these firing neurons. The processed images are capable of inter-active, three-dimensional manipulation and examination. The processed data can be viewed in real time and also be compared via a relational data base management system (RDBMS), through the Internet, to similar data existing in international medical and research databases for analysis and diagnosis.

What is claimed is:

1. A mobile in vivo infrared brain scan system, comprising:
   a helmet with a plurality of infrared (IR) probes, each of the IR probes having an quantum well IR photodetector capable of detecting IR radiation generated by evoked potentials within a user's skull, whereby while wearing the helmet, a user can collect in vivo brain data;
   a plurality of mounting cap assemblies attached with the helmet, such that each of the IR probes is affixed with the helmet using a corresponding mounting cap assembly, each mounting cap assembly housing a pressure-apparatus that is in contact with an IR probe and that is formed to force the IR probe away from the mounting cap assembly and toward a user's scalp; and further comprising:
      a cold finger attached with the quantum well IR photodetector and a cold source passing through the mounting cap assembly and attached with the cold finger to cool the cold finger and thereby cool the quantum well IR photodetector; and
      a cold filter attached with the IR probe such that a space of evacuated volume exists between the quantum well IR photodetector and the cold filter.

2. The brain scan system as set forth in claim 1, wherein the helmet further comprises shock absorbing pads and a chin strap to stabilize the helmet while worn by a user.

3. The brain scan system as set forth in claim 2, wherein the IR probe further includes an optical window in alignment with the quantum well IR photodetector for passing IR radiation to the quantum well IR photodetector, wherein the optical window is capable of transmitting IR radiation.

4. The brain scan system as set forth in claim 3, wherein the IR probe is configured to acquire the brain data and send it along signal wires to a Signal Processor and Transmitter, and wherein the helmet further comprises an antenna, with the Signal Processor and Transmitter being operable for converting the brain data into an analog signal and transmitting the brain data wirelessly using the antenna.

5. The brain scan system as set forth in claim 4, wherein the Signal Processor and Transmitter includes a radio frequency (RF) transmitter and is formed to wirelessly transmit the brain data as an RF signal to a data analysis subsystem.

6. The brain scan system as set forth in claim 5, further comprising a data analysis subsystem, the data analysis subsystem being configured to receive the wirelessly transmitted brain data from the helmet with a plurality of infrared (IR) probes, the brain data being reflective of firing neurons in a mobile subject, and wherein the data analysis subsystem is further configured to generate and display a three-dimensional image that depicts a location of the firing neurons.

7. The brain scan system system as set forth in claim 6, wherein the data analysis subsystem is further configured to:
   compare the brain data against a library of brain data to detect an anomaly in the brain data, the anomaly being indicative of an abnormal brain function; and
   notify a user of any anomaly that is detected in the brain data.

8. The brain scan system as set forth in claim 7, wherein the data analysis subsystem further comprises:
   a receiver system, the receiver system being configured to receive the transmitted brain data as transmitted by the Signal Processor and Transmitter;
   a data processing system, the data processing system having a relational database management system (RDBMS) controller for connecting with and operating an RDBMS, the RDBMS having the library of brain data, and further being configured to receive the brain data from the receiver system and compare the brain data to the RDBMS to detect an anomaly in the brain data.

9. The brain scan system as set forth in claim 8, wherein the data analysis subsystem is further configured to compare the anomaly detected in the brain data with an RDBMS to generate a diagnosis of the anomaly.

10. The brain scan system as set forth in claim 9, wherein the data analysis subsystem is further configured to compare the three-dimensional image with a RDBMS having a library of three-dimensional images to detect the anomaly in the brain data.

11. The brain scan system as set forth in claim 1, wherein the IR probe further includes an optical window in alignment with the quantum well IR photodetector for passing IR radiation to the quantum well IR photodetector, wherein the optical window is capable of transmitting IR radiation.

12. The brain scan system as set forth in claim 1, wherein the IR probe is configured to acquire the brain data and send it along signal wires to a Signal Processor and Transmitter, and wherein the helmet further comprises an antenna, with the Signal Processor and Transmitter being operable for converting the brain data into an analog signal and transmitting the brain data wirelessly using the antenna.

13. The brain scan system as set forth in claim 12, wherein the Signal Processor and Transmitter includes a radio frequency (RF) transmitter and is formed to wirelessly transmit the brain data as an RF signal to a data analysis subsystem.

14. The brain scan system as set forth in claim 1, further comprising a data analysis subsystem, the data analysis subsystem being configured to receive the brain data from the helmet with a plurality of infrared (IR) probes, the brain data being reflective of firing neurons in a mobile subject, and wherein the data analysis subsystem is further configured to generate and display a three-dimensional image that depicts a location of the firing neurons.

15. The brain scan system system as set forth in claim 14, wherein the data analysis subsystem is further configured to:
   compare the brain data against a library of brain data to detect an anomaly in the brain data, the anomaly being indicative of an abnormal brain function; and
   notify a user of the anomaly that is detected in the brain data.

16. The brain scan system as set forth in claim 14, wherein the data analysis subsystem further comprises:
   a receiver system, the receiver system being configured to receive the transmitted brain data from the helmet with a plurality of infrared (IR) probes;
   a data processing system, the data processing system having a relational database management system (RDBMS) controller for connecting with and operating an RDBMS having a library of brain data, and further being configured to receive the brain data from the receiver system and compare the brain data to the RDBMS to detect an anomaly in the brain data.

17. The brain scan system as set forth in claim 16, wherein the data analysis subsystem is further configured to compare the anomaly that is detected in the brain data with an RDBMS to generate a diagnosis of the anomaly.

18. The brain scan system as set forth in claim 14, wherein the data analysis subsystem is further configured to compare the three-dimensional image with a RDBMS having a library of three-dimensional images to detect the anomaly in the brain data.

* * * * *